United States Patent [19]

Crippen

[11] Patent Number: 5,468,219
[45] Date of Patent: Nov. 21, 1995

[54] POROUS FIBERGLASS CAST SYSTEM FOR THE SETTING OF BROKEN APPENDAGES

[76] Inventor: Warren S. Crippen, 50 Georgian Village, Castleknock, Dublin 15, Ireland

[21] Appl. No.: 838,168

[22] Filed: Feb. 20, 1992

[51] Int. Cl.⁶ .................................................. A61F 5/00
[52] U.S. Cl. .................................................. 602/6; 602/8
[58] Field of Search .................................. 602/1, 2, 5, 6, 602/7, 8, 12, 14, 20, 21, 22, 44, 60, 78

[56] References Cited

U.S. PATENT DOCUMENTS

| | | | |
|---|---|---|---|
| 2,853,067 | 9/1958 | Puharich | 602/8 |
| 3,935,355 | 1/1976 | Kuhn | 602/6 |
| 4,215,687 | 8/1980 | Shaw | 128/DIG. 15 |
| 4,492,225 | 1/1985 | Picolet | 602/5 |
| 4,766,890 | 8/1988 | Hollrah | 602/14 |
| 4,888,225 | 12/1989 | Sardvig | 602/8 |
| 5,015,251 | 5/1991 | Cherubini | 128/DIG. 15 |
| 5,076,288 | 12/1991 | Millard | 128/DIG. 15 |

Primary Examiner—Michael A. Brown
Attorney, Agent, or Firm—Walter G. Finch

[57] ABSTRACT

A porous fiberglass cast system for the setting of broken appendages is herein provided. The present invention uses a simplified technique involving a standard fiberglass bandage typical in most cast Systems. Fastening strips impregnated with a curable resin are sewn or woven in rows along the width of one side and down the length of the other side of the unimpregnated fiberglass bandage. Upon wrapping the bandage to an injured member, the fastening strips overlap and produce a cross-mesh. The nature of the fastening strips allows this cross mesh to initially stabilize the structure during cementing. After curing is complete, the intersecting points of the fastening strips in the cross mesh provide a rigidified cross-mesh structure strong enough to completely immobilize the injured member. The areas contained in the cross-meshing between the fastening strips, not being impregnated with any kind of resin, retain their porosity once the cast is cured. Consequently, these areas become the avenues for moisture evaporation and air circulation, thereby greatly reducing discomfort to the wearer.

10 Claims, 2 Drawing Sheets

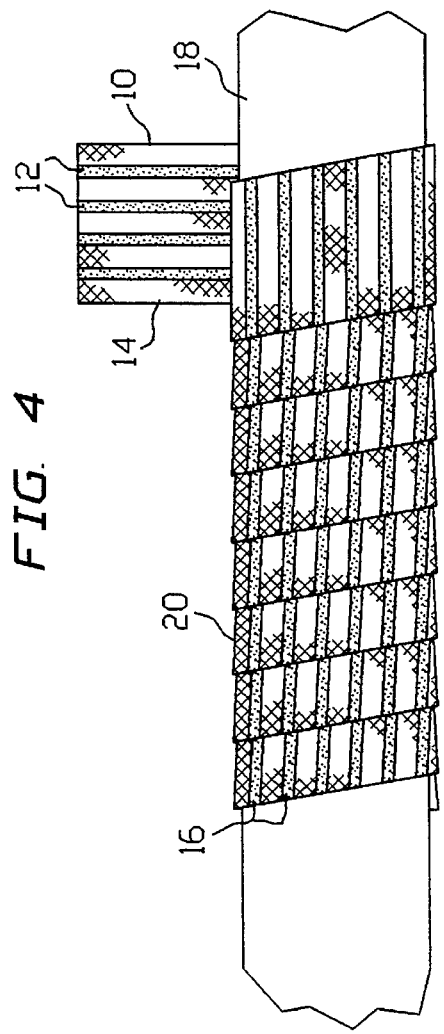
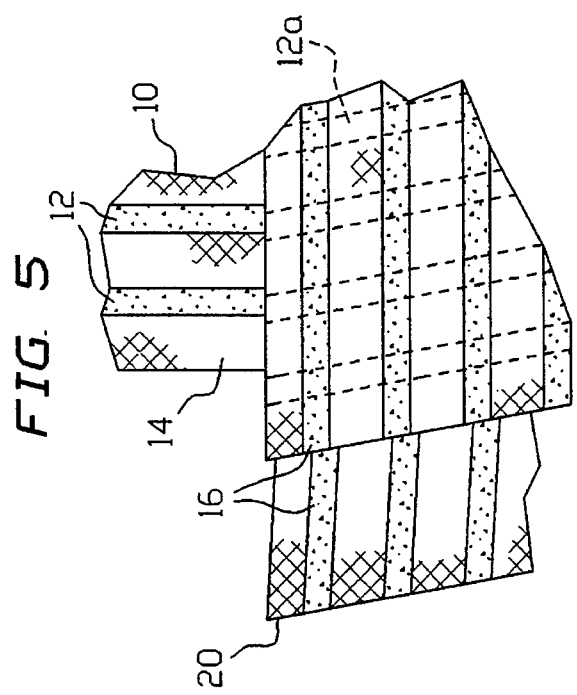

POROUS FIBERGLASS CAST SYSTEM FOR THE SETTING OF BROKEN APPENDAGES

BACKGROUND OF THE INVENTION

This invention relates to a novel porous fiberglass cast system for the setting of broken appendages, whereby the finished and cured cast is of sufficient strength and rigidity to immobilize the appendage while maintaining a high level of porosity throughout the cast structure.

BEST KNOWN PRIOR ART

The best known prior U.S. art is as follows:

3,881,473-Corvi
4,103,682-Franzl
4,173,131-Pendergrass
4,194,041-Gore
4,235,228-Gaylord
4,238,522-Potts
4,320,750-Dabroski
4,627,424-Baron
4,827,916-Kosova
4,841,958-Ersfeld
4,926,848-Shimkus
4,989,593-Campagna
5,016,622-Norvell Other references include:
DT 2,324,456
JO 2,001,284-A
"Glass Plastic Cast", Anderson, et al.

The art of casting is filled with concepts which revolve around the notion that a cast, one cured, should demonstrate good air permeability if it is going to be comfortable to the user. The U.S. Pat. No. 3,881,473 issued to Corvi, et al. describes a lightweight, air permeable, and non-irritating textile of interknit or interwoven glass fabric yarns. Similarly, the Baron, et al U.S. Pat. No. 4,627,424 teaches of a bandage material for forming an orthopedic cast comprising a pliant, large mesh fabric carrier formed from a knit of high strength fiberglass yarn which, when formed into its final shape, exhibits high sturdiness as well as good porosity in order that the underlying skin may breathe.

The Pendergrass, et al. U.S. Pat. No. 4,173,131 introduces a lightweight porous elastic bandage consisting of false twist synthetic yarns with a filling inlay of regular yarns. The U.S. Pat. No. 4,238,522 issued to Potts teaches of a bandage material produced from a crosslinked copolymer of a lactone monomer and a polyfunctional acrylate monomer, which in one embodiment, produces a porous, rigid, and lightweight orthopedic cast.

West German Patent No. 2,324,456 describes a perforated splint insert for plaster bandages that forms a cavity between body and bandage. In U.S. Pat. No. 4,827,916 Kosova reveals a novel vent for use in an orthopedic cast which provides ventilation in casts where poor air circulation may result in overheating, general discomfort, and skin irritation or deterioration caused from an excess build up of bacteria. Franzl, in U.S. Pat. No. 4,103,682, introduces a simplified appendage immobilizing device consisting of a rigid and perforated supporting member lined with a non-allergenic material.

Another important features of casts is their resistance to water. In the accompanying literature, Anderson, M.D. et al. discuss a lightweight, water resistant, and porous bandage composed of 20% glass and 80% cellulose acetate (by weight) which, made into a cast, forms a strong yet comfortable mesh open to the circulation of water vapor and air.

In U.S. Pat. No. 4,320,750 issued to Dabroski, improved water resistant properties for a plaster of paris cast are discussed. Similarly, the Ersfeld, et al. U.S. Pat. No. 4,841,958 teaches a non-woven fabric casting material consisting of resin coated fibers and substantially unoccluded apertures between the fibers which, in operational use, and permits sufficient water vapor permeability and thus avoids skin irritation.

Certain casting systems are specially made to readily remove moisture within the cast into the outside atmosphere. Such is the case with the Gaylord, Jr., et al. U.S. Pat. No. 4,235,228 which describes an orthopedic cast material fabricated from a hydrophobic textile. In operational use, it transfers moisture from the skin of the wearer to the surface of the cast material where the moisture readily evaporates, thus alleviating skin irritation and odor beneath the cast.

In a similar manner, the Campagna, et al. U.S. Pat. No. 4,989,593 teaches an orthopedic cast including a padding that is treated with a fluorochemical or silicone. The padding is thus able to shed water rapidly, thus providing comfort to the user. Consequently, this system allows bathing or discretionary exposure to water which would not otherwise be permitted.

A number of castings boast the ability to be impermeable to water but permeable to water vapor. This is the case in the JO Patent 2,001,284 which introduces a new casting material formed from a porous plastic of a polyolefin resin which, while following the molten of the applied body part, displays both water vapor permeability and water impermeability, thus alleviating stuffiness and rashes.

A three layered water permeable/water vapor impermeable orthopedic cast consisting of an inner protective sleeve permitting perspiration, water, or urine to vaporize away, a second layer of soft padding, and a final outer layer of an immobilizing plaster of paris or other organic polymer resin/glass fiber composite splinting material is the subject of Norvell U.S. Pat. No. 5,016,622. The U.S. Pat. No. 4,194,041 issued to Gore, et al. teaches of a waterproof laminate which prevents liquids from penetrating to undergarments but allows moisture vapor such as perspiration to escape.

The Shimkus, et al. U.S. Pat. No. 4,926,848 discusses an elastic strip useful as a bandage which incorporates VELCRO™ attachment components.

The art has, however, does not provide a casting system which incorporates a simplified VELCRO™ type attachment system which not only serves to provide a rigid cross-mesh structure capable of immobilizing the injured member when the cast is cured, but also to keep the entire structure stabilized during the curing process. Also, a high level of porosity throughout the cast structure has not been achieved as the result of the using of a rigidified cross-meshing structure to contain the appendage.

OBJECTS OF THE INVENTION

It is an object of this invention to provide a fiberglass cast system for the setting of broken appendages.

Another object of this invention is to provide a simplified fiberglass cast system whose unique configuration of materials provides a sufficiently rigid yet comfortably porous cast structure.

Still another object of this invention is to provide a novel fiberglass cast system whose rigid mesh is the result of having thin fastening strips impregnated with a curable resin sewn or woven on to both sides of a standard fiberglass bandage made of a woven fiberglass fabric, such as that used in a typical cast.

To eliminate discomfort to the wearer of the cast by leaving a relatively large area of the supporting bandage porous, is still another object of this invention.

To provide adequate air circulation to and around the injured member contained within the cast, thereby permitting excess heat to be dissipated and inner moisture to be evaporated, is yet another object of this invention.

And to provide a support means for the immobilization of injured members consisting of a porous fiberglass cast system whose interlocking mesh is capable of restricting the motion of appendages yet whose overall structure is sufficiently porous so as to provide a comforting degree of air circulation to the wearer, is another object of this invention.

BRIEF DESCRIPTION OF THE DRAWINGS

These and other attendant advantages of this invention will become more obvious and apparent in the following detailed specification and accompanying drawings in which:

FIG. 4 is a comprehensive view of the technique involved in wrapping an injured appendage with the fiberglass bandage of FIG. 1; and FIG. 5 is an enlarged view of a detail of FIG. 4.

DESCRIPTION OF THE PREFERRED EMBODIMENTS OF THE INVENTION

Referring now to FIGS. 1 to 5 of the drawings, there is shown the preferred embodiment of the invention of a casting system based on the use of a standard fiberglass bandage 14.

Figure 3:
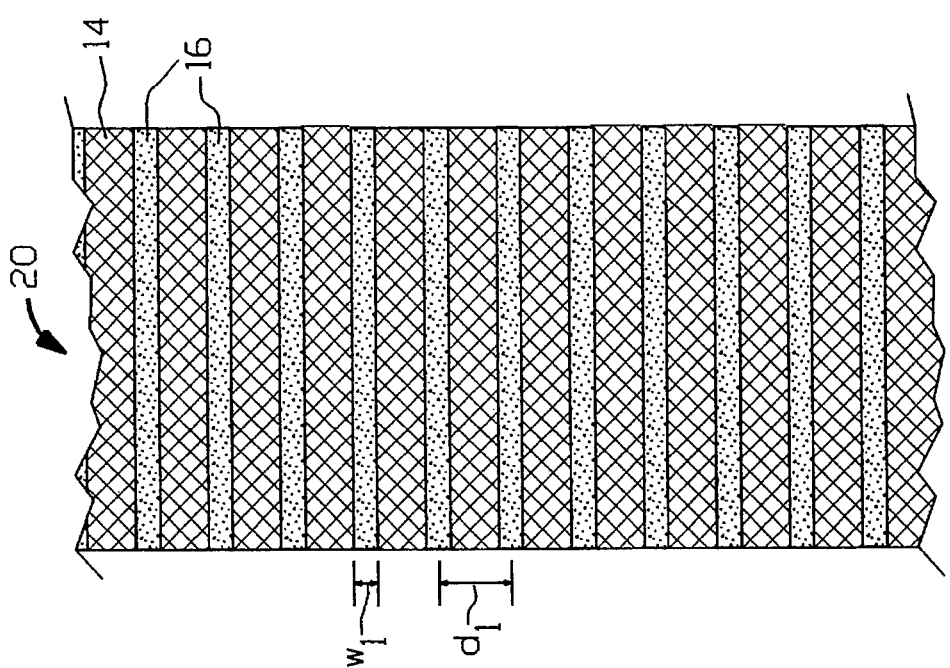
FIG. 3 is a rear view of the fiberglass bandage of FIG. 1.

Presented in FIG. 3 is the front side 20 of the fiberglass bandage 14. On this side, fastening strips 16 such as VEL-CRO™ or another similar material run across the width of the fiberglass bandage 14. These fastening strips 16, having been impregnated with a curable resin, are sewn or woven along the width of the front side 20 of the bandage 14. The fastening strips 16 have a width $w_1$ of approximately ⅛ of an inch and a center to center spacing $d_1$ of approximately ⅜ of an inch.

Figure 1:
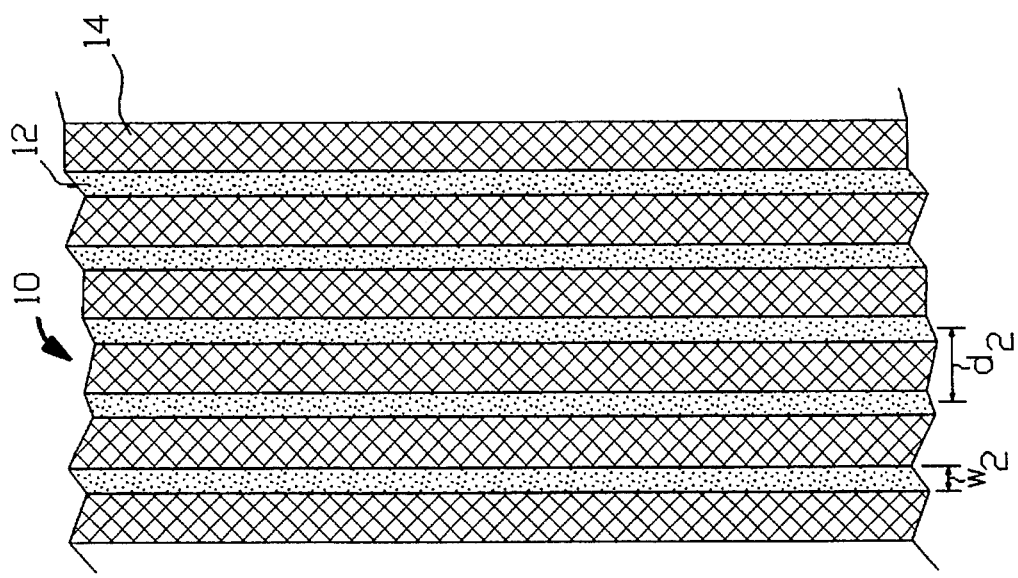
FIG. 1 is a front view of a fiberglass bandage incorporating features of this invention.

FIG. 1 depicts other side 10 of the fiberglass bandage 14. On this rear side 10, impregnated fastening strips 12 identical to those on the front side 20 of the fiberglass bandage 14 are also sewn and woven to, but this time along the length of, the bandage 14. These fastening strips 12 also have a width $w_2$ of approximately ⅛ of an inch and a center to center spacing $d_2$ of approximately ⅜ of an inch.

Figure 2:
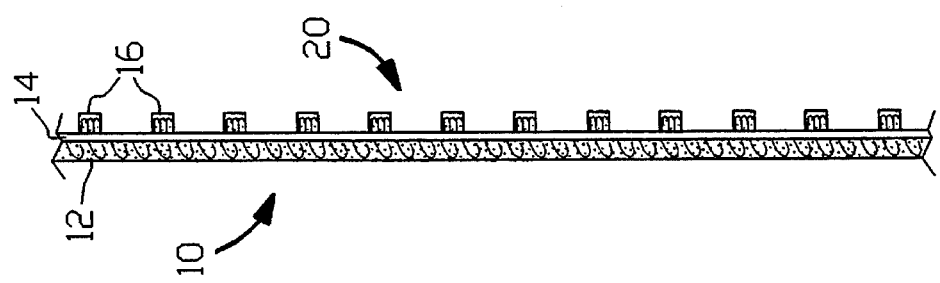
FIG. 2 is an edge view of the longitudinal axis of the bandage of FIG. 1.

FIG. 2 is an edge view of the longitudinal axis of the fiberglass bandage 14. Multiple fastening strips 16 can be viewed running across the width of the front face 20 of the fiberglass bandage 14. On the rear side 10 of the bandage 14, the first fastening strip 12 running down the length of the fiberglass bandage 14 obstructs the view of the other fastening strips 12 behind it.

The fastening strips 12, 16 serve two primary purposes. The application of the bandage 14 to the injured member is such that the fastening strips 12, 16 form a cross mesh when wrapped over each other. Consequently, their first function is to hold the entire system in place while the cementing action occurs.

Their second function is manifest once curing is complete. The intersecting points formed by the overlapping fastening strips 12, 16 produce a rigidified cross mesh binding structure that will provide the required stiffness and strength to immobilize the injured member while healing. In another embodiment, the fastening strips 12, 16 may be reinforced with strands of wire 22 from either metal or synthetic like Teflon™ to assure the strength and support required for the structure.

An illustration of the application of the fiberglass bandage 14 to a broken appendage 18 is given in FIG. 4. The bandage 14 is spirally wound on to the appendage 18 so that the front side 20 of the bandage 14 faces outwardly, while the rear side 10 of the bandage 14 faces inward. Subsequently, the fastening strips 12 on the rear side 10 overlay at nearly right angles on to the fastening strips 16 on the front side 20, thereby producing an interconnected cross mesh.

FIG. 5 further illustrates this cross mesh by indicating the relative connection of the underlying fastening strips 12a on the rear side of the bandage 14 to the fastening strips 16 on the front side 20 of the bandage 14. Since only the fastening strips 12, 16 have been impregnated with a curable resin activated by an appropriate stimulus (and not the fiberglass bandage itself 14), the areas between these fastening strips 12, 16 remain porous even after curing is complete. Consequently, these porous areas formed between the cross-mesh of fastening strips 12, 16 become the avenues through which heat may dissipate and water may evaporate, thereby providing the wearer with a comfortable yet rigid cast structure.

In another embodiment of the invention, the fastening strips 12, 16 may be attached to the front 20 and rear 10 sides of the bandage 14 at specified angles. This new fastening strip orientation allows the cross-mesh created by the overlapping of the fastening strips 12, 16 to take shapes other than that illustrated in FIG. 5 and to subsequently attain different physical properties.

Modifications and variations of the present invention are possible in light of the above teachings. It is, therefore, to be understood that within the scope of the appended claims, the invention may be practiced otherwise than as specifically described.

What is claimed is:

1. A support means for an injured or broken appendage, comprising, a woven fiberglass fabric bandage, having interengaging fastening strips attached to a front face and a rear face respectively of said woven fiberglass fabric bandage, wherein said interengaging fastening strips are either sewn or woven respectively across the width of said front face of said fiberglass bandage and down the length of said rear face of said fiberglass bandage.

2. A support means for an injured or broken appendage as in claim 1, whereby said interengaging fastening strips are positioned in a spaced apart relationship on said front face and said back face of said woven fiberglass fabric bandage.

3. A support means for an injured of broken appendage as in claim 1, wherein said interengaging fastening strips are impregnated with a curable resin prior to attachment to said woven fiberglass fabric bandage.

4. A support means for an injured or broken appendage as in claim 3, whereby upon applying said woven fiberglass fabric bandage to an injured member, said interengaging fastening strips overlap by nature of their respective orientation on to each other to form a connective cross-mesh and hold said woven fiberglass fabric bandage stationary until curing is complete.

5. A support means for an injured or broken appendage as in claim 4, wherein upon completion of curing, a plurality of intersecting points of said interengaging fastening strips forming said connective cross-mesh provide an overall cured cast structure with the strength and rigidity to immobilize said injured member.

6. A support means for an injured or broken appendage as in claim 4, wherein said connective cross-mesh formed within said overall cured cast structure contains numerous areas of porous woven fiberglass fabric bandage capable of air circulation and moisture evaporation.

7. A support means for an injured or broken appendage as in claim 6, wherein said porous areas between said interengaging fastening strips of said rigid cross-mesh become the avenues through which heat and moisture internal to said overall cured cast structure may dissipate and evaporate, respectively, thereby promoting comfort to a wearer.

8. A support means for an injured or broken appendage as in claim 3, wherein said interengaging fastening strips may be attached to both said front face and said rear face respectively of said woven fiberglass fabric bandage at various specific angles or orientations and thereby, upon wrapping said woven fiberglass fabric bandage to said injured member, provide uniquely shaped cross-meshes with different physical properties which, upon curing, produce a strong yet porous structure capable of restricting motion of said appendage while allowing air circulation to and around said appendage.

9. A support means for an injured or broken appendage as in claim 1, wherein said interengaging fastening strips may be further supported by the addition of strands of wire from metal thereby adding strength without sacrificing porosity to an overall cast structure.

10. A support means for an injured or broken appendage as in claim 1, wherein said interengaging fastening strips may be further supported by the addition of strands of non-metallic wire.

* * * * *